United States Patent
Berner (10) Patent No.: US 10,759,706 B2
(45) Date of Patent: Sep. 1, 2020

(54) BODY MADE OF A CERAMIC MATERIAL

(71) Applicant: STRAUMANN HOLDING AG, Basel (CH)

(72) Inventor: Simon Berner, Suhr (CH)

(73) Assignee: STRAUMANN HOLDING AG, Basel (CH)

(*) Notice: Subject to any disclaimer, the term of this patent is extended or adjusted under 35 U.S.C. 154(b) by 376 days.

(21) Appl. No.: 14/654,567

(22) PCT Filed: Dec. 23, 2013

(86) PCT No.: PCT/EP2013/003902
§ 371 (c)(1),
(2) Date: Jun. 22, 2015

(87) PCT Pub. No.: WO2014/101998
PCT Pub. Date: Jul. 3, 2014

(65) Prior Publication Data
US 2015/0299049 A1  Oct. 22, 2015

(30) Foreign Application Priority Data
Dec. 24, 2012 (EP) .................................. 12008609

(51) Int. Cl.
*C04B 35/48* (2006.01)
*A61C 8/00* (2006.01)
(Continued)

(52) U.S. Cl.
CPC ............ *C04B 35/48* (2013.01); *A61C 8/0012* (2013.01); *A61K 6/818* (2020.01); *C04B 35/117* (2013.01);
(Continued)

(58) Field of Classification Search
CPC .......... C04B 41/5042; C04B 2103/001; C04B 41/4556; C04B 35/48; C04B 41/009;
(Continued)

(56) References Cited

U.S. PATENT DOCUMENTS

| 4,525,464 A | * | 6/1985 | Claussen ............. C04B 35/4885 264/662 |
| RE32,449 E | | 6/1987 | Claussen et al. |

(Continued)

FOREIGN PATENT DOCUMENTS

| EP | 1 600 176 A1 | 11/2005 | |
| EP | 1600176 A1 | * 11/2005 | ............. A61L 27/10 |

(Continued)

OTHER PUBLICATIONS

Apr. 24, 2014 International Search Report issued in International Application No. PCT/EP2013/003902.
(Continued)

*Primary Examiner* — Alicia J Sawdon
(74) *Attorney, Agent, or Firm* — Oliff PLC (57) ABSTRACT

A body made of a ceramic material having a surface region extending from the surface of the body to a predetermined depth and a core region being integrally formed with the surface region. The ceramic material in the surface region includes a calcium containing crystalline phase.

18 Claims, 3 Drawing Sheets

(51) Int. Cl.
  *C04B 35/488* (2006.01)
  *C04B 41/87* (2006.01)
  *C04B 41/50* (2006.01)
  *C04B 35/117* (2006.01)
  *C04B 35/119* (2006.01)
  *C04B 41/00* (2006.01)
  *A61K 6/818* (2020.01)
  *C04B 41/53* (2006.01)
  *C04B 41/88* (2006.01)
  *C04B 111/00* (2006.01)

(52) U.S. Cl.
  CPC .......... *C04B 35/119* (2013.01); *C04B 35/488* (2013.01); *C04B 41/009* (2013.01); *C04B 41/5042* (2013.01); *C04B 41/5338* (2013.01); *C04B 41/87* (2013.01); *C04B 41/88* (2013.01); *C04B 2111/00836* (2013.01); *C04B 2235/3208* (2013.01); *C04B 2235/3225* (2013.01); *C04B 2235/3246* (2013.01); *C04B 2235/3248* (2013.01); *C04B 2235/442* (2013.01); *C04B 2235/443* (2013.01); *C04B 2235/65* (2013.01); *C04B 2235/75* (2013.01); *C04B 2235/775* (2013.01); *C04B 2235/96* (2013.01); *C04B 2235/963* (2013.01); *C04B 2235/9669* (2013.01)

(58) Field of Classification Search
  CPC ............ C04B 41/4535; C04B 41/4545; C04B 2111/00836; C04B 2235/3208; C04B 2235/3225; C04B 2235/3246; C04B 2235/3248; C04B 2235/442; C04B 2235/443; C04B 2235/65; C04B 2235/75; C04B 2235/775; C04B 2235/96; C04B 2235/963; C04B 2235/9669; C04B 35/117; C04B 35/119; C04B 35/488; C04B 41/5338; C04B 41/87; C04B 41/88; A61C 8/0012; A61K 6/024
  See application file for complete search history.

(56) References Cited

U.S. PATENT DOCUMENTS

| | | | | |
|---|---|---|---|---|
| 5,125,971 | A | * | 6/1992 | Nonami .............. A61C 8/0012 106/35 |
| 2009/0118114 | A1 | * | 5/2009 | Zhang .................... A61L 27/10 501/135 |
| 2009/0191280 | A1 | * | 7/2009 | Kokubo ................ A61L 27/025 424/617 |
| 2010/0179665 | A1 | * | 7/2010 | Schlottig ............. A61C 8/0012 623/23.53 |
| 2011/0318582 | A1 | * | 12/2011 | Dittmann ............ C04B 35/6281 428/402 |
| 2012/0071986 | A1 | | 3/2012 | Anitua Aldecoa et al. |
| 2013/0011610 | A1 | * | 1/2013 | Stephan ................ C04B 41/515 428/141 |

FOREIGN PATENT DOCUMENTS

| | | | | |
|---|---|---|---|---|
| EP | | 2 371 344 A1 | 10/2011 | |
| EP | | 2371344 A1 | * 10/2011 | .......... C04B 41/009 |
| JP | | 2004-075532 A | 3/2004 | |
| WO | | 2012/175218 A1 | 12/2012 | |

OTHER PUBLICATIONS

Apr. 24, 2014 Written Opinion issued in International Application No. PCT/EP2013/003902.

* cited by examiner

BODY MADE OF A CERAMIC MATERIAL

The present invention relates to a body made of a ceramic material, according to the preamble of claim 1, to a process for preparing said body, according to the preamble of claim 11, and to the use of the body as an implant, in particular a dental implant, or an abutment for such an implant.

Dental implants generally comprise an anchoring part, which is designed to be anchored in the jaw bone, and a mounting part, which serves as a base for the direct or indirect attachment of a suprastructure, such as a crown or bridge.

There are one-part dental implant systems, in which the anchoring part and the mounting part are integrally formed of one piece, and two-part dental implant systems, comprising a separate piece, the so-called "abutment", serving as a mounting part.

An abutment is thus a separate mounting part for a dental implant, intended for connecting the part that is anchored in the bone to the suprastructure.

Dental implants which are currently in use are in general made of a metal, e.g. titanium, or a ceramic, e.g. a zirconia based ceramic.

In contrast to metal implants, which are dark and therefore mismatch with the color of natural teeth, ceramic materials have the advantage that their color can be closely matched to the natural tooth color. Efforts have thus been made to provide dental implants, of which at least the parts that are visible after insertion are made of a ceramic material.

Despite their favourable properties with regard to the color, the use of ceramic materials for dental implants is in many cases limited by their fatigue stability, which is generally rather low.

A ceramic material having a high mechanical strength is disclosed in U.S. Pat. No. 6,165,925, which relates to an yttrium oxide-stabilized zirconium oxide in predominantly tetragonal form (yttria-stabilized tetragonal zirconia; Y-TZP) for the production of a sintered semi-finished article.

Despite its favourable mechanical properties, in particular its high strength, toughness and wear resistance, Y-TZP has, however, a propensity to low-temperature degradation (LTD) in the presence of moisture, as for example described by Chevalier et al., J. Am. Ceram. Soc., 92 (9), 1901-1920 (2009).

Low-temperature degradation is a kinetic phenomenon in which polycrystalline tetragonal zirconia transforms to monoclinic zirconia over a rather narrow but important temperature range, typically from room temperature to about 400° C.

The degradation progresses from the surface of the material to its interior and is accompanied by micro- and macrocracking, thus resulting in reduced fracture strength of the material.

This problem, which is also referred to as "low hydrothermal stability", is particularly relevant for the use of zirconia for a dental implant, since a dental implant is after implantation exposed to a humid and warm environment and needs to fulfil relatively strict safety requirements over a long period.

In addition, dental implants are often subjected to a subtractive treatment in order to improve its osteointegrative properties. In this regard, EP-A-1 982 670, for example, relates to a process for providing a topography to the surface of a dental implant made of a ceramic material, wherein at least a part of the surface is etched with an etching solution comprising hydrofluoric acid. Etching of the ceramic material has, however, been found to often go along with a further deterioration of its hydrothermal stability.

For improving its hydrothermal stability, it has been suggested to dope yttria-stabilized zirconia with a suitable amount of ceria. In this regard, it is referred to Huang et al. Journal of the European Ceramic Society 25 (2005), pp. 3109-3115 and to Settu et al., Journal of the European Ceramic Society 16 (1996), pp. 1309 to 1318, both referring to yttria-ceria-stabilized zirconia.

Yttria-ceria-stabilized zirconia has, however, the disadvantage that it is darker in colour than yttria-stabilized zirconia. This is particularly disadvantageous if the material is used for a dental implant, which preferably has a light colour matching with the natural tooth colour. Further, yttria-ceria-stabilized zirconia has the disadvantage that it is not suitable for being Thus, the strength obtainable for yttria-ceria-stabilized zirconia is lower compared to yttria-stabilized zirconia.

Alternatively, a homogenous dispersion of $Al_2O_3$ grains into a tetragonal yttria-stabilized zirconia matrix has been reported to increase the hydrothermal stability of the tetragonal phase, as for example stated in the above mentioned article of Huang et al. However, also the doping with alumina has a negative impact on the translucency of yttria-stabilized zirconia.

Considering the shortcomings of known stabilized ceramic materials, and in particular yttria-stabilized zirconia, the problem of the present invention is thus to provide a body made of a ceramic material, said body having an improved hydrothermal stability, i.e. an improved long-term stability under warm and humid conditions, by maintaining the mechanical and visual properties of the ceramic material on which the body is based.

The object is achieved by the body according to claim 1. Preferred embodiments are given in the dependent claims.

The present invention thus relates to a body made of a ceramic material. According to the invention, the body comprises a surface region extending from the surface of the body to a predetermined depth and a core region being integrally formed with the surface region.

In other words, the surface region and the core region are formed in a continuous material formation. There is, thus, no discrete interface between the core region and the surface region, as it would be the case if the surface region is in the form of a discrete layer or coating applied on the core region.

The ceramic material in the surface region comprises a calcium containing crystalline phase. In other words, the ceramic material in the surface region comprises a crystal phase having a structure which comprises calcium atoms as part of the crystal lattice. Thus, at least a portion of the calcium atoms and/or ions present in the surface region are—as part of the ceramic material—arranged in an array of points repeating periodically in three dimensions.

In general, the ceramic material in the surface region of the body of the present invention is not uniformly crystalline, but rather comprises islands of the calcium containing crystalline phase surrounded by material of a different phase, which can be amorphous or crystalline.

Preferably, the body is made of a ceramic material comprising alumina and/or zirconia. More preferably, the ceramic material is based on yttria-stabilized zirconia.

According to a particularly preferred embodiment, the ceramic material in the surface region comprises a Ca—Zr—O phase, and even more particularly a crystalline phase of the system $CaO$—$ZrO_2$, such as $CaZr_4O_9$ or $CaZrO_3$, as will be shown in more detail below. Preferably, this calcium containing phase is surrounded by zirconia in tetragonal phase, more preferably yttria-stabilized zirconia in tetragonal phase.

Due to the feature of the ceramic material comprising a calcium containing crystalline phase, and, thus, calcium atoms as part of the crystal lattice, the body of the present invention is in any respect different from a body containing calcium solely in amorphous form. The calcium containing crystalline phase according to the present invention is further different from a calcium-stabilized phase in which calcium atoms are not arranged periodically.

It has surprisingly been found that the body of the present invention has a higher hydrothermal stability than a body without a calcium containing crystalline phase in the surface region. Hydrothermal aging effects, which might ultimately lead to a reduced fracture strength of the body, can thus be diminished or fully eliminated by the present invention.

The increase in hydrothermal stability is particularly pronounced if the ceramic material is based on yttria-stabilized zirconia in tetragonal phase. This is at least partly due to the fact that by the formation of a calcium containing crystalline phase at least a portion of the tetragonal phase, which intrinsically has a relatively high tendency for low temperature degradation, is transformed into a phase of higher hydrothermal stability.

Further, the formation of a calcium containing crystalline phase having a lower theoretical density than the phase on which it is based goes along with a volume increase with respect to basic phase, thus building up a compressive stress within the surface region which ultimately results in an increased flexural strength of the body.

The present invention thus allows to increase the flexural strength of e.g. zirconia in tetragonal phase, which is often preferred due to its ability to undergo martensitic transformation and, thus, to respond to induced stress, namely to close cracks and/or to countervail crack propagation in the body.

Preferably, the theoretical density of the calcium containing crystalline phase is also lower than the one of zirconia in monoclinic phase, which has a lower density than the respective tetragonal phase. Thus, even after back-transformation from the monoclinic phase to the tetragonal phase, which can be induced by a heat treatment and which goes along with a volume decrease, an increase in the flexural strength of the body can be achieved by the formation of the calcium containing crystalline phase.

If both the calcium containing crystalline phase and zirconia in tetragonal phase are present in the surface region, a body having a high hydrothermal stability and a high flexural strength can be achieved which simultaneously has the ability to undergo martensitic transformation and, thus, to respond to induced stress, namely to close cracks and/or to countervail crack propagation in the body.

As mentioned, the core region and the surface region of the body are integrally formed with each other, although these regions have in general a different structural constitution. In other words, there is according to the present invention a gradual transition from the core region to the surface region. This is in contrast to a step-wise transition, as it is the case when the regions are not integrally form, e.g. when the surface region is in the form of a separate coating of an additional material applied on a core body. Consequently, there is according to the present invention no splitting off of the calcium containing crystalline phase, as it is typically seen for a separate coating.

Typically, the proportion of calcium of the ceramic material decreases continuously in direction from the surface to the core region, as will be discussed in detail by way of the examples below.

The above mentioned embodiment, in which the proportion of calcium in the ceramic material decreases continuously in direction from the surface to the core region, also includes embodiments of the body, in which the decrease starts from a given depth and having in its outermost region a constant proportion of calcium.

The term "proportion" as used in this context relates to the atomic percentage or molar percentage of calcium in atomic or ionic form, respectively, relative to the total number of atoms/ions or molecules, respectively, of the ceramic material. The chemical composition of the surface region, and specifically the decrease of the calcium proportion in the surface region, can for example be determined by X-ray Photoelectron Spectroscopy (XPS) in a manner well known to the skilled person.

As will be shown in detail below, the crystal structure of the ceramic material in the surface region of the body is typically such that the content of monoclinic phase is lower than in the respective region of a body devoid of a calcium containing crystalline phase, in particular after having exposed the body to a humid and warm environment.

The term "content" as used in this context relates to the volume percentage of the respective crystalline phase relative to the total volume of all detectable phases, more specifically all phases observed in X-ray diffraction, which is a suitable method for determining the content and which is further specified in the context of the examples given below.

More specifically, the content of monoclinic phase is preferably less than 25%, preferably less than 20%. This is in contrast to known ceramic bodies having no surface region according to the present invention, since the transformation from tetragonal to monoclinic phase typically begins at the surface of the body, as for example explained by the above mentioned article of Chevalier et al. A suitable method for determining the content of monoclinic phase includes X-ray diffraction (XRD) which is well known to the skilled person and further specified in the context of the examples given below.

According to a preferred embodiment, the calcium containing crystalline phase is solely present in the surface region. Thus, the other mechanical properties of the ceramic material—apart from the hydrothermal stability—can be kept essentially unchanged. In particular, the strength, toughness and wear resistance of e.g. yttria-stabilized tetragonal zirconia can be maintained. Also, the visual appearance of the body can be kept essentially unchanged.

According to a further preferred embodiment of the present invention, the surface region extends from the surface of the body to a depth of at least 5 nm, more preferably at least 10 nm, even more preferably at least 30 nm and most preferably at least 50 nm, thus providing an especially high hydrothermal stability.

It is further preferred that the surface region extends from the surface of the body to a depth of at most 200 µm, more preferably at most 10 µm, even more preferably at most 5 µm, and most preferably at most 1 µm. This allows the high hydrothermal stability to be achieved without interfering substantially with the mechanical properties of the body, as e.g. achieved by surface roughening.

According to a particularly preferred embodiment, the surface region extends to a depth ranging from about 5 nm to about 200 µm, more preferably about 10 nm to about 10

μm, even more preferably from about 30 nm to about 5 μm and most preferably from about 50 nm to about 1 μm.

As will be explained in detail below, the formation of a calcium containing crystalline phase can be achieved by a very straightforward process comprising the steps of applying at least one calcium compound onto the surface of a basic ceramic body and thermally treating the basic ceramic body with the calcium compound applied thereon at a temperature of at least 500° C. Thereby, a calcium component based on the calcium compound diffuses into the basic ceramic body in an amount sufficient that a calcium containing crystalline phase is formed.

The basic body is typically prepared by a sintering process. Sintering processes for achieving a ceramic body, and in particular a ceramic dental implant, are well known to a skilled person.

In order to provide good interaction with the surrounding tissue, and in particular highly osteointegrative properties to the body, which is of particular relevance if the latter is used as a dental implant, at least a part of the surface of the body has a roughened surface.

As will be pointed out by way of the examples, the technical effect achieved by the present invention, i.e. a increased hydrothermal stability, is particularly pronounced when the surface of the body or a part thereof is machined.

According to a further preferred embodiment, the body is made of a ceramic material comprising alumina and/or zirconia, as mentioned above.

With regard to a ceramic material comprising zirconia, it is particularly preferred that the calcium containing crystalline phase is a Ca—Zr—O phase, i.e. a phase which contains calcium, zirconium and oxygen. It is especially preferred that the calcium containing crystalline phase is a CaO—$ZrO_2$ phase, and more preferably is selected from the group consisting of a monoclinic $CaZr_4O_9$ phase, a cubic $CaZrO_3$ phase and an orthorhombic $CaZrO_3$ phase. It is thereby particularly preferred that the calcium containing crystalline phase is an orthorhombic $CaZrO_3$ phase, since the presence of this phase has been shown to go along with a specifically high hydrothermal stability.

For an orthorhombic $CaZrO_3$ phase to be formed, a relatively high amount of calcium or its oxide, respectively, in the surface region is required.

In this regard, it is preferred that the amount of CaO in the surface region preferably ranges from about 3 mol-% to about 50 mol-%, more preferably from about 6 mol-% to about 50 mol-%, and most preferably from about 15 mol-% to about 30 mol-%. In this context, mol-% refers to the number of CaO versus the sum of CaO and $ZrO_2$ of the material of the surface region.

The CaO—$ZrO_2$ crystalline phase can further contain minor amounts of yttrium and/or hafnium, as known to the skilled person. It is understood that these crystalline phases are also encompassed by the terms "Ca—Zr—O phase" and "CaO—$ZrO_2$ phase".

In general, the ceramic material is stabilized by a stabilizing agent. Specifically, the stabilizing agent is preferably selected from the group of yttrium, cerium and their respective oxides. Additionally or alternatively, the stabilizing agent can be magnesium, calcium, strontium, ytterbium, gadolinium and/or neodymium or their respective oxides.

More specifically, the body of the present invention is preferably made of a ceramic material comprising yttria-stabilized zirconia. In general, the yttria-stabilized zirconia used is tetragonal in phase. As mentioned above, yttria-stabilized tetragonal zirconia has a very high strength, a high toughness, a good wear resistance and further the ability to undergo martensitic transformation. In addition, the material has a light colour which can be closely adapted to natural tooth colour.

Other stabilized ceramic materials, such as an alumina based ceramic material, to which the present invention also relates, are known to the skilled person. In this regard, the skilled person is also aware of stabilizing agents other than the ones mentioned above. For example, calcium, magnesium, indium, lanthanum and/or scandium (and mixtures thereof) as well as their respective oxides can be used as a stabilizing agent, depending on the ceramic material used and the purpose to be achieved.

Further stabilizing agents include for example $Ga^{3+}$, which is also mentioned in the article of Chevalier referenced above. All these stabilizing agents are encompassed by the term "stabilizing agent" used in the context of the present invention.

Apart from the body defined above, the present invention further relates to a process for preparing the body, said process comprising the steps of applying at least one calcium compound onto the surface of a basic ceramic body and thermally treating the basic ceramic body with the calcium compound applied thereon at a temperature of at least 500° C.

Thereby, a calcium containing crystalline phase is formed in a surface region of the body.

As mentioned above, the basic body is preferably made of a ceramic material comprising yttria-stabilized zirconia, but in no way limited thereto. The basic body is typically prepared by a sintering process known to the skilled person.

In order to achieve a sufficient diffusion of calcium into the body and thus a formation of the calcium containing crystalline phase, a sufficient temperature is preferably chosen.

The actual temperature and heating time of the treatment depends on the specific ceramic material and the depth of the surface region to be achieved. A person skilled in the art who has become aware of the present invention knows how to set this temperature.

In the context of the present invention the term "calcium compound" is used for the calcium species applied onto the ceramic body, whereas the term "calcium component" is used for the calcium species that diffuses into the ceramic body and is thereby integrated in the surface region of the body.

Since Ca ions or CaO is the preferred component to diffuse into the ceramic body, the calcium compound to be applied onto the surface of the basic ceramic body is preferably a compound which in the course of the thermal treatment forms CaO. Further, calcium ions are likewise preferred to diffuse into the ceramic body. According to a particularly preferred embodiment, a calcium salt selected from the group of $Ca(HCO_3)_2$, $CaCO_3$ and $Ca(NO_3)_2$ is used.

The application of the calcium compound, such as CaO, $Ca(OH)_2$, $Ca(HCO_3)_2$, $Ca(NO_3)_2$ or $CaCO_3$, can be carried out by e.g. soaking/immersion, dipping or drop casting into a respective suspension or emulsion, a sol-gel-process, by a process using a slurry, by embedding into powder, e.g. when using $CaCO_3$, by the use of spin coating, electrophoresis, sandblasting, or by plasma immersion ion implantation (PIII).

It has been found that by applying a calcium containing gel or paste, e.g. a $CaCO_3$ containing paste, a particularly high amount of the calcium component diffusing into the body can be achieved. The application of a calcium containing gel or paste is particularly preferred, since thereby the formation of a Ca—Zr—O containing phase, in particular a $CaZrO_3$ phase, more particularly an orthorhombic $CaZrO_3$ phase, in the surface region of the body can be achieved. In this embodiment, the content of monoclinic phase in the surface region is very low, if not 0, and a very high hydrothermal stability is achieved. As will be shown by way of the examples, the application of a calcium containing gel allows a very high hydrothermal stability to be achieved even if the basic ceramic body has been subjected to a sand-blasting and etching treatment.

Alternatively to the method described above, other methods for the application of the calcium compound include physical vapour deposition (PVD), chemical vapour deposition (CVD) and atomic layer deposition (ALD).

Given the fact that the calcium component diffuses into the ceramic material, there is no discrete coating. An interfacial area, as present in the case of a discrete coating, is thus diminished or even eliminated by the present invention Consequently, there is no splitting or washing off of the calcium component, as it is typically seen when a separate coating of an additional material is applied on a ceramic body.

The calcium component being integrated into the material of the body is in clear contrast to the teaching of EP-A-1847278, relating to titanium and thus to a material for which a diffusion of a calcium component by the thermal treatment according to step b) would not be obtained.

Diffusion of the calcium component together with a stabilizing agent, specifically yttrium or yttria, is particularly preferred. According to a particularly preferred embodiment, a stabilizing agent, specifically yttrium or yttria, is applied onto the surface of the basic ceramic body in addition to calcium containing compound, said stabilizing agent diffusing into the basic ceramic body by thermal treatment.

In this context, the calcium containing compound and the stabilizing agent can be applied in two separate steps or simultaneously.

If they are applied in two separate steps, the stabilizing agent can either be applied before or after applying the calcium containing compound.

Further, they can be applied by different methods of application. For example, the stabilizing agent, specifically yttrium or yttria, can be applied by physical vapour deposition, followed by the application of the calcium containing compound by soaking/immersion into a respective suspension.

It is further possible to apply either one of the calcium containing compound and the stabilizing agent in a first step, followed by a first thermal treatment in order to perform diffusion into the ceramic basic body in a second step, then apply the other one of the calcium containing compound and the stabilizing agent, i.e. the one not applied in the first step, in a third step, followed by a second thermal treatment in order to perform diffusion into the ceramic basic body in a fourth step. In this regard, the temperature of the first thermal treatment and the temperature of the second thermal treatment can be different.

Most surprisingly, it has been found that by using both the calcium component and yttrium (or yttria) in the process, the calcium component diffuses deeper into the ceramic material than if no yttrium/yttria is co-diffused.

As mentioned above, a particularly good interaction of the body with the surrounding tissue, and specifically an increase in its osteointegrative properties, can be achieved by providing a surface roughness to the body. This is of particular relevance if the body is used as a dental implant.

The process for providing a surface roughness typically includes etching of the surface, which for known ceramic bodies might lead to a deterioration of the hydrothermal stability of the body. In this context, it is referred to Journal of the American Ceramic Society, 69 [7] 583-84 (1986), according to which in acidic solutions, the selective dissolution of yttrium components is accelerated because yttrium ion is more basic than zirconium ion.

As mentioned, the present invention allows the deterioration of the hydrothermal stability to be reversed by forming a calcium containing crystalline phase. It has surprisingly been found that by the process of the present invention, the surface topography of the (basic ceramic) body remains unaltered or is altered in a very minor manner; properties allowing a good interaction with the surrounding tissue, and specifically the osteointegrative properties achieved by the surface roughening are thus not affected by the process of the present invention.

According to the present invention, the process thus preferably comprises the step of roughening at least a part of the surface of the basic body by a subtractive treatment before applying the calcium compound.

A subtractive treatment comprising a machining step is particularly preferred, since the respective process leads to a particularly high hydrothermal stability.

Alternatively or additionally, the subtractive treatment comprises an etching step. It is thereby particularly preferred that the etching step is carried out with an etching solution comprising hydrofluoric acid at a temperature of at least 70° C. By this treatment, discrete grains or agglomerates of grains are removed from the bulk ceramic material, whereby a surface having recesses and cavities is formed, thus leading to a "microscopic" surface roughness. A detailed description of this etching step is given in EP-A-1982670, in particular paragraphs [0024] to [0030] , [0060] to [0064] and [0079] to [0081], the disclosure of which is hereby incorporated by reference.

It is further preferred that the subtractive treatment further comprises a sand-blasting step prior to the etching step. Thereby, a "macroscopic" surface roughness is obtained, which in combination with the "microscopic" surface roughness mentioned above further contributes to the good interaction with the surrounding tissue, and specifically the high osteointegrative properties of the body.

According to a particularly preferred embodiment, the surface topography is defined by the arithmetic mean height Sa (3D roughness parameter) being in a range from 0.1 µm and 1.7 µm, preferably being in a range from 0.3 µm to 0.9 µm, more preferably from 0.5 µm to 0.75 µm. Methods for determining Sa are well known to the skilled person; an exemplary description of its determination is further given below.

It has been found that for a body made of a ceramic material, a particularly strong interaction with the surrounding tissue, specifically the bone tissue, can be achieved if the surface topography falls within the above definition.

Preferably, the surface topography is further defined by the skewness of the height distribution $S_{sk}$ (3D roughness parameter) being in a range from −0.6 to 0.6, preferably from −0.4 to 0.6, more preferably from −0.3 to 0.5. Methods for determining $S_{sk}$ are well known to the skilled person; an exemplary description of its determination is further given below.

Preferably, the surface topography is further defined by a developed surface area Sdr being in a range from 5% to 40%, preferably in a range from 10% to 30%. Sdr is measured in % enlargement compared to a totally plane reference area which equals to the measured area. Sdr is in the art also referred to as interfacial area and methods for its determination are well known to the skilled person.

As mentioned, the determination of surface topography parameters is well known to the skilled person.

According to one specific example, measurement is carried out using a confocal microscope (μsurf explorer, Nano-Focus AG, Oberhausen, Germany) with the following specifications:

Light source: green LED (wavelength 505 nm);
Scan mode: piezoelectric scanner; 0.59 μm interval between subsequent images of the image stack;
Object lens: 20× (working distance 3.1 mm, numerical aperture 0.45);
Field of view: 798 μm×798 μm (512×512 data points); and
Lateral resolution: 1.56 μm; and
Ultimate vertical resolution: 5 nm.

The roughness parameter can for example be determined using the following:

Software: WinSAM, Version 2.6.07 (University of Erlangen-Nürnberg);
Filter: Moving-average Gaussian filter with a cut-off wavelength of x=31 μm, y=30 μm (20×19 image points), subsequent plane subtraction; and
KFL-analysis: Limits from the amplitude density, 10 nm increments. As mentioned, the body of the present invention is prepared using a sintering process. It is in this regard thinkable that method step a), i.e. the application of the calcium compound, is performed on the (pre-sintered) white body, which is afterwards subjected to the final sintering temperature and thus simultaneously also to the thermal treatment according to step b).

This process is particularly suitable if a relatively great depth of diffusion is to be achieved, in particular for improving the body's resistance to hydrothermal aging.

According to a particularly preferred embodiment, a zirconia ceramic body is pre-sintered at about 1350° C. for about 2 hours, then covered with a $CaCO_3$ powder followed by final sintering at about 1450° C. for about 2 hours.

According to a further preferred embodiment of the invention, the thermal treatment is followed by cleaning the dental implant of non-specifically bonded, residual calcium compound. This cleaning step is preferably performed by rinsing the dental implant with pure water or an aqueous solution like e.g. NaCl solution, or another liquid. In particular if the calcium compound applied is in solid form, e.g. as $CaCO_3$ powder, other cleaning methods, such as air streaming, brushing and/or polishing can be performed for the removal.

The performance of the washing step can be improved by using ultrasound or acid washing. Thereby, grains, grain agglomerates or reaction products which loosely adhere to the surface are effectively removed.

In view of the process described above, the present invention also relates to a body obtainable by said process.

In addition, all preferred features mentioned for the body of the present invention likewise apply to the process of the present invention and vice versa.

As mentioned above, the object achieved by the present invention is particularly useful in the field of implantology, in particular in oral implantology. The present invention thus further relates to the use of the body as an implant, in particular a dental implant.

The present invention likewise relates to the use of the body as an abutment for such an implant. All features and advantages mentioned above for an implant, in particular a dental implant, likewise apply to an abutment.

The present invention is further illustrated by way of the following examples:

EXAMPLES

Example 1

Discs of pressed $ZrO_2$ (Tosoh-Zirconia TZ-3YSB-E) were pre-sintered at a temperature of 1350° C. for 2 hours in a sintering oven (Nabertherm; including a slow temperature increase with a holding time of 2 hours at 600° C.). The resulting pre-sintered discs were then covered with $CaCO_3$ powder by putting the discs into an $Al_2O_3$ dish and sprinkling the $CaCO_3$ powder onto them through a sieve (about 15 mg per disc). Final sintering was then carried out at 1450° C. for 2 hours.

Powder residues were then brushed off the treated discs before rinsing them with ultrapure water.

The discs were dried under a stream of argon.

Normalized Atomic Concentration Determined by X-Ray Photoelectron Spectroscopy (XPS)

Figure 1:
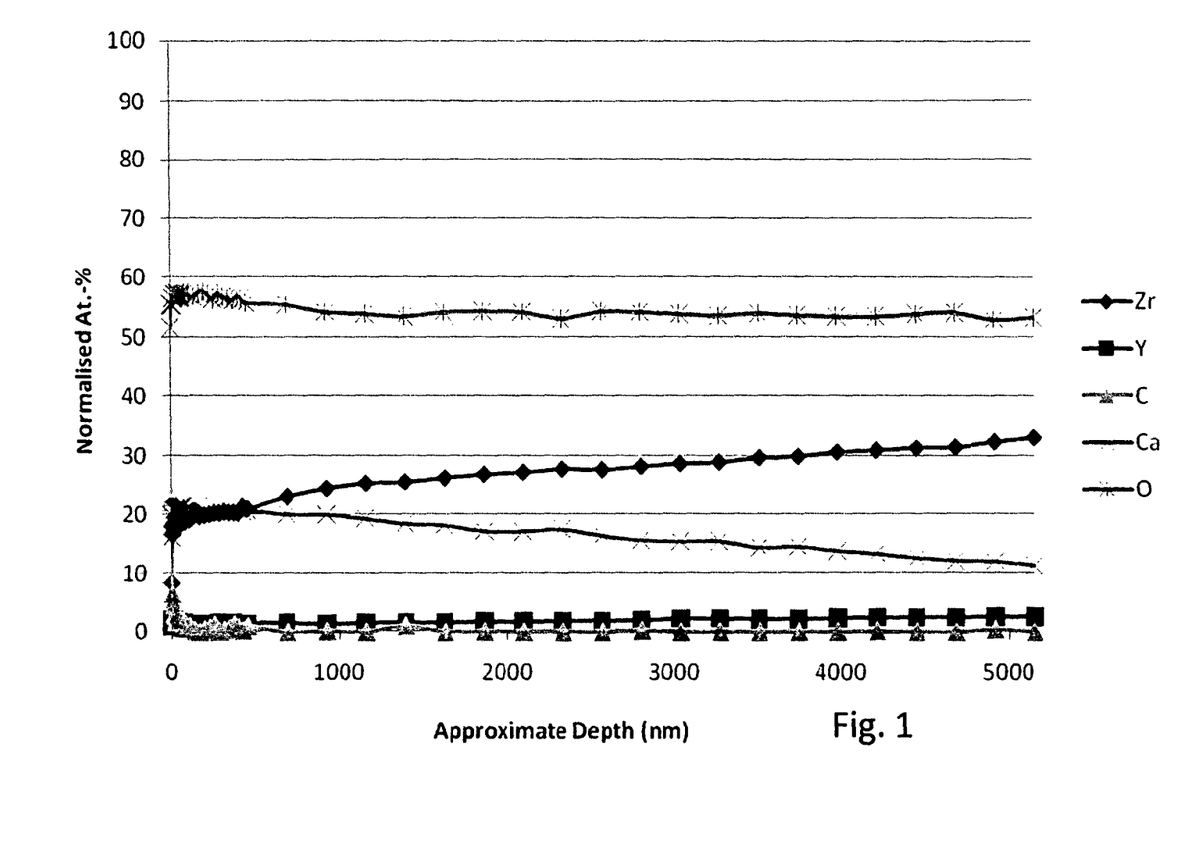
FIG. 1 shows a graphical representation of the normalized atomic concentration of the elements (Zr, Y, C, Ca and O) comprised in the body obtained according to the Example 1 in relation to the depth of the body.

As will be shown by way of the Figures, XPS measurement of the discs according to Example 1 revealed that even at a depth of 5 μm the material has a normalized atomic concentration of calcium of more than 10% and that calcium is present even at a depth of about 10 μm.

The results can be explained by a thermally induced diffusion of calcium into the ceramic material of the basic body.

Analysis of Crystal Structure by X-Ray Diffraction (XRD)

In order to determine the crystal structure, the discs were further analysed by X-ray diffraction (XRD) using a diffractometer of the type Empyrean (PANalytical) in the ϑ/ϑ-constellation (radiation source: Cu (40 kV/40 mA); range of incidence angle: 20° to 70°; step width: 0.026°; measuring time per measuring point: 300 s).

XRD measurement revealed three different phases, namely a monoclinic $CaZr_4O_9$ phase, a cubic $CaZrO_3$ phase and an orthorhombic $CaZrO_3$ phase, in the contents given below:

| Phase | Content/% |
|---|---|
| $CaZr_4O_9$ (monoclinic) | 23.7 |
| $CaZrO_3$ (cubic) | 6.0 |
| $CaZrO_3$ (orthorhombic) | 70.3 |

Example 2

Discs of yttria-stabilized zirconia (MZ111 HIP of CeramTec AG) having a machined surface, a thickness of about 1 mm and a diameter of about 5 mm were used.

The discs were then machined, before they were cleaned with Deconex 15 PF for 5 minutes using ultra-sound and subjected to a plasma treatment. Specifically, the plasma treatment was performed using an apparatus of the type "Femto" (Diener Electronics GmbH+Co. KG, Ebhausen) using the following parameters: power 35 W, 6 sccm oxygen gas flow (sccm: standard cubic centimeter per minute; 1 sccm cm3 per minute at normal pressure, i.e. 1013 mbar), pressure≈0.1 mbar, time 2.5 minutes).

A 20 mM solution of $Ca(HCO_3)_2$ was prepared by preparing a 20 mM $Ca(OH)_2$ solution, sterile-filtering the latter and introducing $CO_2$ into the solution, upon which the solution becomes turbid ($CaCO_3$) and finally turns again into a clear solution.

20 µl of the $Ca(HCO_3)_2$ was pipetted on the surface of the disc (diameter 5 mm), heated to 950° C. for 2 hours and then cooled in air. The samples were then rinsed using pure water and dried under a stream of argon.

As reference example, a disc of yttria-stabilized zirconia as specified above but without further treatment (sample 2B) was provided. The reference example was stored in air.

Example 3

Further examples (samples 3A and 3B) have been prepared using the $Ca(HCO_3)_2$ solution in analogy to Example 2, but by sand-blasting and etching the discs (instead of machining).

As a further difference to Example 2, the discs have been heated to 1150° C. for 2 hours (sample 3A) and 3 hours (sample 3B), respectively (instead of 950° C. for 2 hours).

Example 4

A still further example (sample 4) has been prepared in analogy to sample 3B, but by applying a $CaCO_3$ paste (instead of a $Ca(HCO_3)_2$ solution) before the heat treatment (1150° C. for 3 hours).

To this end, a $CaCO_3$ paste was prepared by mixing $CaCO_3$ with water in a weight ratio of 1:1, and, after the plasma treatment, applied to the discs in a thickness of about 2 mm.

Example 5

A still further example (sample 5) has been prepared by in analogy to sample 3A, but by applying a calcium containing gel (instead of a $Ca(HCO_3)_2$ solution) before the heat treatment (1150° C. for 2 hours).

To this end, a Ca containing gel consisting of $Ca(NO_3)_2$, PVA (polyvinyl alcohol, 20 kD molecular weight) and water was prepared. Specifically, solutions of 20 wt-% PVA and 20 wt-% $Ca(NO_3)_2 \cdot 4H_2O$ were prepared with water and mixed at a ratio of 1:1. After the plasma treatment, the gel was applied to the discs in a thickness of about 2 mm.

Hydrothermal aging of the samples 2A, 2B, 2C, 3A, 3B, 4 and 5 was simulated by autoclaving them up to 22 hours at 120° C. and at 135° C., respectively, using an autoclave of the type Systec DE-56.

The hydrothermal stability of the samples was then examined by determining the content of monoclinic phase (specifically after 20 hours at 120° C., and after 5 hours and 22 hours at 135° C. for the first test series, and after 5 hours and 20 hours at 120° C. as well as after 20 hours at 135° C. for the second test series). This determination was carried out by X-ray diffraction using a diffractometer of the type Empyrean (PANalytical) in the $\vartheta/\vartheta$-constellation (radiation source: Cu (40 kV/40 mA); range of incidence angle: 20° to 70°; step width: 0.026°; measuring time per measuring point: 300 s).

As shown in FIG. 1, the material of the body according to Example 1 shows at a depth of 5 µm a normalized atomic concentration of calcium of more than 10%; by extrapolation, it can be concluded that calcium is present even at a depth of about 10 µm.

Figure 2:
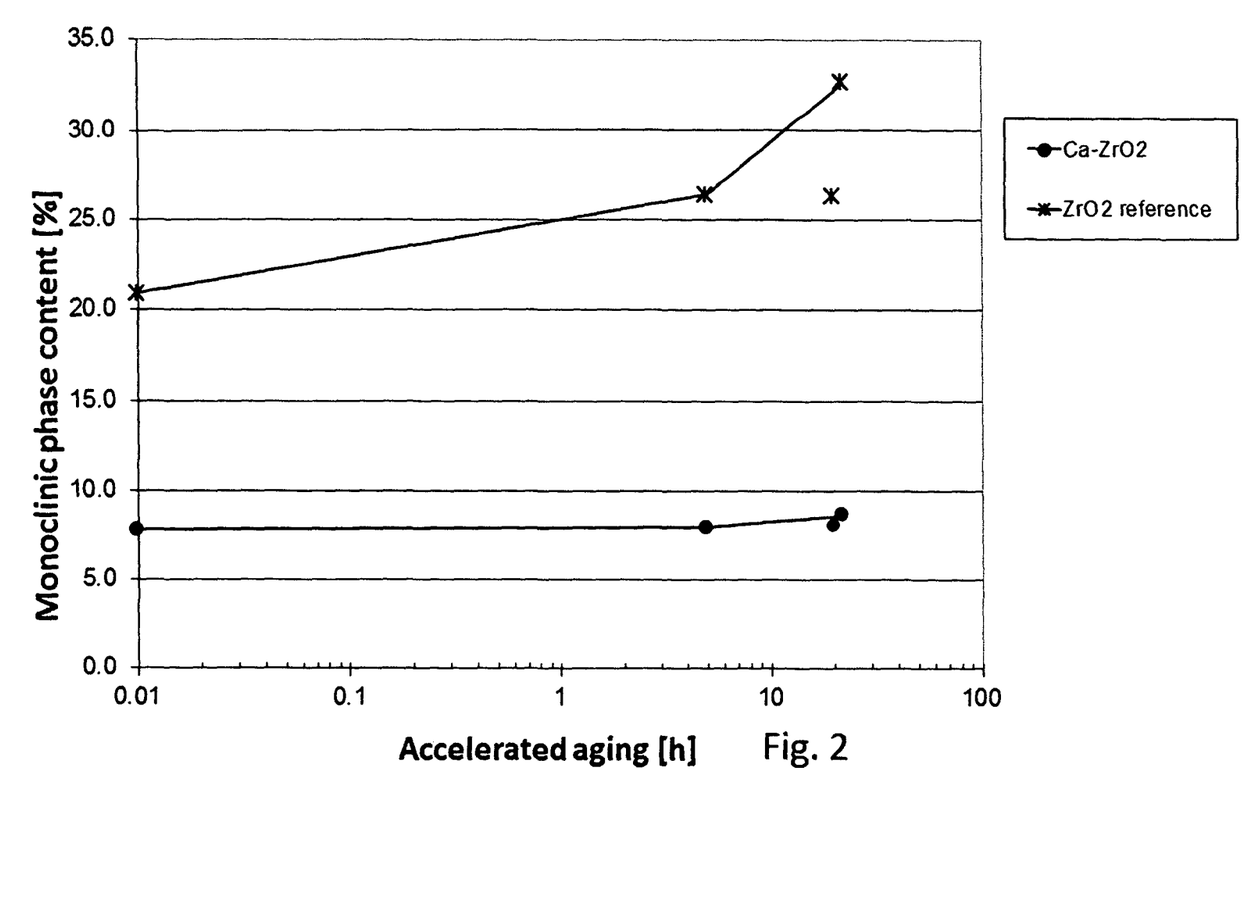
FIG. 2 shows a graphical representation of the content of monoclinic phase as a function of the duration of a simulated aging treatment for a machined ceramic body according to the present invention (sample 2A, referred to as "Ca—$ZrO_2$") in comparison to a reference example (sample 2B, referred to as "$ZrO_2$ reference")

The body of the present invention shows almost no hydrothermal aging, as shown in FIG. 2. Specifically, the content of the monoclinic phase is for sample 2A lower than 10% even after subjecting the sample to 135° C. for 22 hours. Thus, the requirement according to ISO 13356 that the content of monoclinic phase is less than 25% after simulated aging at 135° C. for 5 hours is fully met.

This is in contrast to reference sample 2B. Sample 2B shows a lower initial hydrothermal stability and a relatively fast decrease in the hydrothermal stability.

Figure 3:
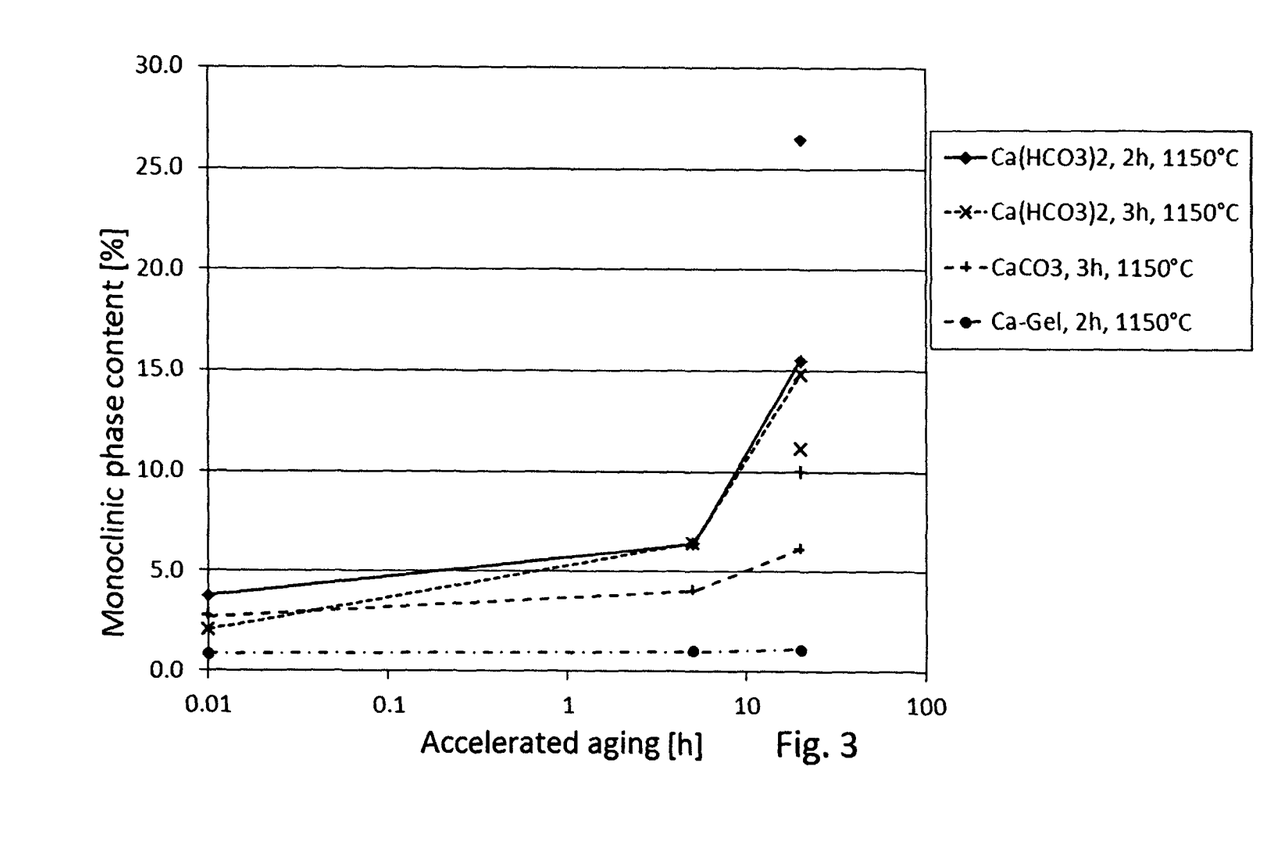
FIG. 3 shows a graphical representation of the content of monoclinic phase as a function of the duration of a simulated aging treatment for a number of sand-blasted and etched ceramic bodies according to samples 3A (referred to as "$Ca(HCO_2)_2$, 2 h, 1150° C."), 3B (referred to as "$Ca(HCO_3)_2$, 3 h, 1150° C."), 4 (referred to as "$CaCO_3$, 3 h, 1150° C.") and 5 (referred to as "Ca-Gel, 2 h, 1150° C.") of the present invention.

As shown in FIG. 3, almost no formation of monoclinic phase was determined for sample 5, for which a calcium containing gel was applied. Regarding hydrothermal stability, this sample showed thus the best results followed by the sample 4 for which only a very minor increase in monoclinic phase could be determined.

The invention claimed is:

1. A body made of a ceramic material comprising zirconia and having a surface region extending from the surface of the body to a predetermined depth and a core region being integrally formed with the surface region,
   wherein the ceramic material in the surface region comprises a calcium containing crystalline phase and an yttrium or yttria stabilizing agent, which is obtained by depositing calcium carbonate as a calcium component and the yttrium or yttria stabilizing agent in one step on a surface of the ceramic material and thermally treating the ceramic material thereby causing co-diffusion of the calcium component and the stabilizing agent,
   wherein the body is an implant or an abutment for an implant, and
   wherein a proportion of calcium of the ceramic material decreases continuously in a direction from the surface of the body to the core region, and
   wherein said thermal treatment is carried out for a temperature and time sufficient to result in a normalized atomic concentration of calcium of at least 10% at a depth of 5 µm.

2. The body according to claim 1, wherein the calcium containing crystalline phase is solely present in the surface region.

3. The body according to claim 1, wherein the crystal structure of the ceramic material in the surface region is such that the content of monoclinic phase is less than 25%.

4. The body according to claim 1, wherein the surface region extends from the surface of the body to a depth of at least 5 nm.

5. The body according to claim 1, wherein the surface region extends from the surface of the body to a depth ranging from 5 nm to 200 µm.

6. The body according to claim 1, wherein at least a part of the surface of the body has a roughened surface.

7. The body according to claim 1, wherein the body is made of a ceramic material additionally comprising alumina.

8. The body according to claim 7, wherein the calcium containing crystalline phase is a Ca—Zr—O phase.

9. The body according to claim 8, wherein the calcium containing crystalline phase is a CaO—$ZrO_2$ phase.

10. The body according to claim 1, wherein the body is made of a ceramic material comprising yttria-stabilized zirconia.

11. The body according to claim 9 wherein the CaO—$ZrO_2$ phase is selected from the group consisting of a monoclinic $CaZr_4O_9$ phase, a cubic $CaZrO_3$ phase and an orthorhombic $CaZrO_3$ phase.

12. The body according to claim 11, wherein the CaO—$ZrO_2$ phase is an orthorhombic $CaZrO_3$ phase.

13. The body of claim 1, wherein the implant or the abutment for an implant is a dental implant, or an abutment for a dental implant.

14. The body of claim 1, wherein the normalized atomic concentration of calcium is at least 20% at the surface.

15. A process for preparing a body according to claim 1, said process comprising the steps of
applying the calcium component and the yttrium or yttria stabilizing agent in one step onto the surface of a basic ceramic body; and
thermally treating the basic ceramic body with the calcium component and yttrium or yttria stabilizing agent applied thereon at a temperature of at least 500° C., whereby the calcium component diffuses into the basic ceramic body in an amount sufficient that a calcium containing crystalline phase is formed.

16. The process according to claim 15, further comprising the step of roughening at least a part of the surface of the basic body by a subtractive treatment before applying the calcium compound.

17. The process according to claim 15, wherein the subtractive treatment comprises an etching step.

18. The body obtained by the process according to claim 15.

* * * * *